United States Patent [19]

Sebastian et al.

[11] Patent Number: 4,703,750

[45] Date of Patent: Nov. 3, 1987

[54] THERAPEUTIC LUMBOSACRAL APPLIANCE

[76] Inventors: Peter R. Sebastian, 919 Loch Lomond Ct., Salisbury, Md. 21801; John L. Stump, 1202 Grande Pointe; Daphne, Ala. 36526

[21] Appl. No.: 901,559

[22] Filed: Aug. 29, 1986

[51] Int. Cl.[4] .............................................. A61F 5/02
[52] U.S. Cl. .......................................... 128/78; 2/338; 2/DIG. 6; 128/DIG. 20
[58] Field of Search ................... 128/78, 24 R, 68, 69, 128/DIG. 20; 2/338, DIG. 6

[56] References Cited

U.S. PATENT DOCUMENTS

| 1,646,590 | 10/1927 | Mildenberg | 128/78 X |
| 2,104,758 | 1/1938 | Poppen | 128/DIG. 20 |
| 2,240,308 | 4/1941 | Mahe | 128/100 X |
| 2,554,337 | 5/1951 | Lampert | 128/78 X |
| 3,071,133 | 1/1963 | Eisen | 128/78 |
| 3,521,623 | 7/1970 | Nichols et al. | 128/78 |
| 3,955,565 | 5/1976 | Johnson, Jr. | 128/DIG. 20 |
| 3,974,827 | 8/1976 | Bodeen | 128/DIG. 20 |
| 4,099,523 | 7/1978 | Lowrey | 128/78 X |
| 4,120,297 | 10/1978 | Rabinschong et al. | 128/78 |
| 4,135,503 | 1/1979 | Ramano | 128/78 |
| 4,175,548 | 11/1979 | Henry | 128/78 X |
| 4,178,922 | 12/1979 | Curlee | 128/78 |
| 4,178,923 | 12/1979 | Curlee | 128/78 |
| 4,475,543 | 10/1984 | Brooks et al. | 128/78 |
| 4,552,135 | 11/1985 | Racz et al. | 128/78 |
| 4,559,933 | 12/1985 | Batard et al. | 128/78 |
| 4,576,154 | 3/1986 | Hyman et al. | 128/78 |
| 4,597,386 | 7/1986 | Goldstein | 128/78 |
| 4,622,957 | 11/1986 | Curlee | 128/78 |

FOREIGN PATENT DOCUMENTS

| 2454702 | 5/1976 | Fed. Rep. of Germany . | |
| 1461408 | 11/1966 | France | 128/78 |
| 985591 | 3/1965 | United Kingdom . | |

Primary Examiner—Edgar S. Burr
Assistant Examiner—Moshe I. Cohen
Attorney, Agent, or Firm—Wenderoth, Lind & Ponack

[57] ABSTRACT

A therapeutic appliance for application to the lumbar spine and which follows the contours of the iliac crests and overlies the sacrum and sacroiliac joints as well as anchors below the posterior superior iliac spines of the human body including an external shell having a length sufficient to extend around the abdominal region of the body with fasteners at opposite ends of the shell and an air bladder disposed on the shell. The air bladder has a plurality of air chambers located centrally between opposite ends of the shell with each of the air chambers being in fluid communication with each other and to an air conduit for inflating them. The air chambers include elongated air chambers which extend transversely to the longitudinal direction of the shell having upper ends substantially parallel to each other and lower ends shaped to lie above the iliac crests. The air chambers also include an elongated air chamber extending in the longitudinal direction disposed between the lower ends of the transversely extending air chambers and an outer edge of the bladder positioned to overlie the sacrum and lie between the sacroiliac joints. The air chambers also include an anchoring air chamber between the longitudinally extending air chamber and the outer edge of the bladder extending arcuately from a central portion of the air bladder towards the opposite ends of the shell positioned to lie below the posterior superior iliac spines to prevent upward riding of the therapeutic appliance when in place on the human body and support for the sacroiliac joints.

20 Claims, 9 Drawing Figures

THERAPEUTIC LUMBOSACRAL APPLIANCE

FIELD OF THE INVENTION

The present invention relates to a lumbosacral therapeutic appliance designed to relieve pain the the areas of the lumbosacral spine and sacroiliac joints by maintaining normal alignment of the osseous structures and providing static stretch to paravertebral muscles to alleviate unwanted muscle spasms and fatigue.

BACKGROUND OF THE INVENTION

The problem of low back pain is commonly a result of mechanical and physiologic derangements of the osseous ligamentous and muscular structures of this region. The low back for purposes of this discussion refers to the area of the lumbar and sacral portions of the spinal column and the sacroiliac joints. The interrelationships between the osseous, ligamentous and muscular structures is highly important in this area of the spine which is responsible for considerable weight bearing and structural support.

Injury to one or more of these three elements commonly results in dysfunction and subsequent pain in the others. Also, injury at one level of the spine may affect adjacent segments leading to dysfunction distant to the original abnormality or site of injury. Proper posture for optimal function is the result of correct vertebral alignment, balanced ligamentous support and limitation of excessive or unwanted movement, and flexibly balanced, strong musculature regulating and stabilizing motion.

While these objectives may be met by a variety of therapeutic modalities, low back braces used for this purpose should have certain characteristics, such as (1) contour fitting of the normal spinal/pelvic curvatures; (2) sufficient firmness to prevent buckling or unwanted binding of the appliance during wearer movement; (3) adequate flexibility to allow free and unrestricted normal range of motion; (4) adequate coverage of anatomically and functionally related segments of the spine where therapeutic forces are needed for maximal effectiveness; and (5) contour shaping of the pelvic segment to avoid unwanted bony bridging effect of the iliac crests which inhibits desired counter pressure over midline and adjacent paravertebral muscles and osseous elements. The prior art therapeutic air inflated appliances fail in one or more of these areas of therapeutic principles.

BRIEF SUMMARY OF THE INVENTION

The present invention provides a new and improved lumbosacral therapeutic appliance designed to relieve pain in the areas of the lumbosacral spine and sacroiliac joints by maintaining normal alignment of the osseous structures and providing static stretch to paravertebral muscles to alleviate unwanted muscle spasms and fatigue. The device of the present invention can perform this function without limitation of the normal motion of the wearer. In addition, this device provides full coverage over the above mentioned structures by being form fitted to the contours of the area while avoiding unwanted bony bridging.

The device of the present invention includes an air bladder contoured to fit among the bony structures by means of central air chambers which overlie the midline of the lumbar spine extending down to the sacrum. The device also includes transversely extending chambers which follow the contour of the iliac crests and longitudinally extended air chambers which overlie the sacrum and lie between the sacroiliac joints as well as air chambers which lie just beneath the posterior superior iliac spines and serve to also anchor and prevent upward riding of the appliance and provide support for the sacroiliac joints.

The device of the present invention also contains a more readily accessible means of altering air chamber pressure through an air conduit/valve mechansim even when the appliance is worn under clothing.

BRIEF DESCRIPTION OF THE DRAWINGS

Details of the invention are shown by the following description of an embodiment with reference to the figures in the drawings, in which are shown:

FIG. 6 is a more detailed view of FIG. 5a.

DETAILED DESCRIPTION OF THE PREFERRED EMBODIMENT

Figure 1:
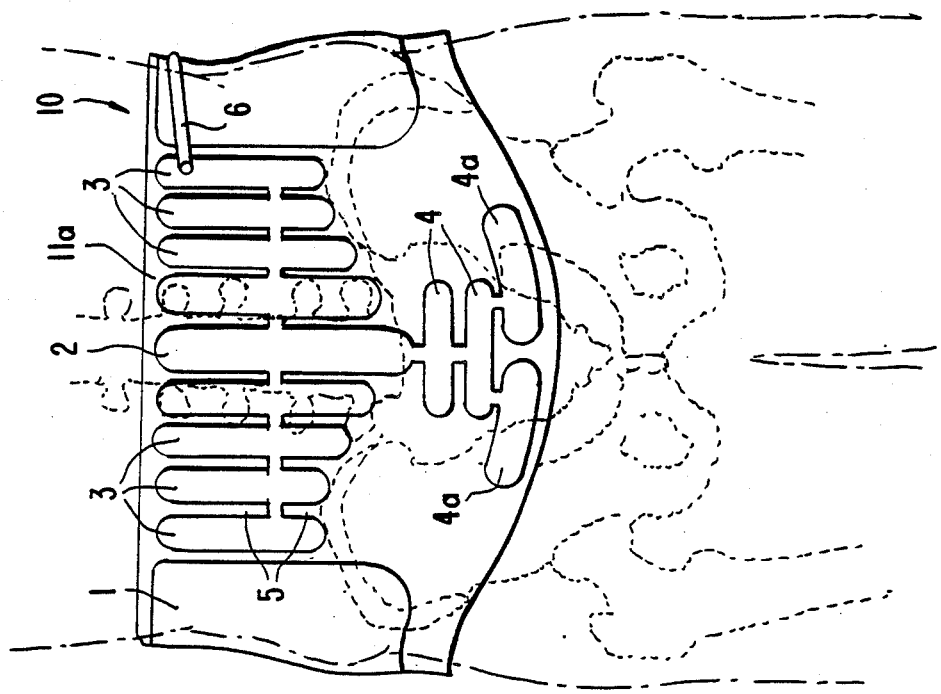
FIG. 1 illustrates the lower part of the throacic spine, the lumbar spine, the sacrum, the sacroiliac joints, the iliac crests and the posterior superior iliac spine.
Figure 2:
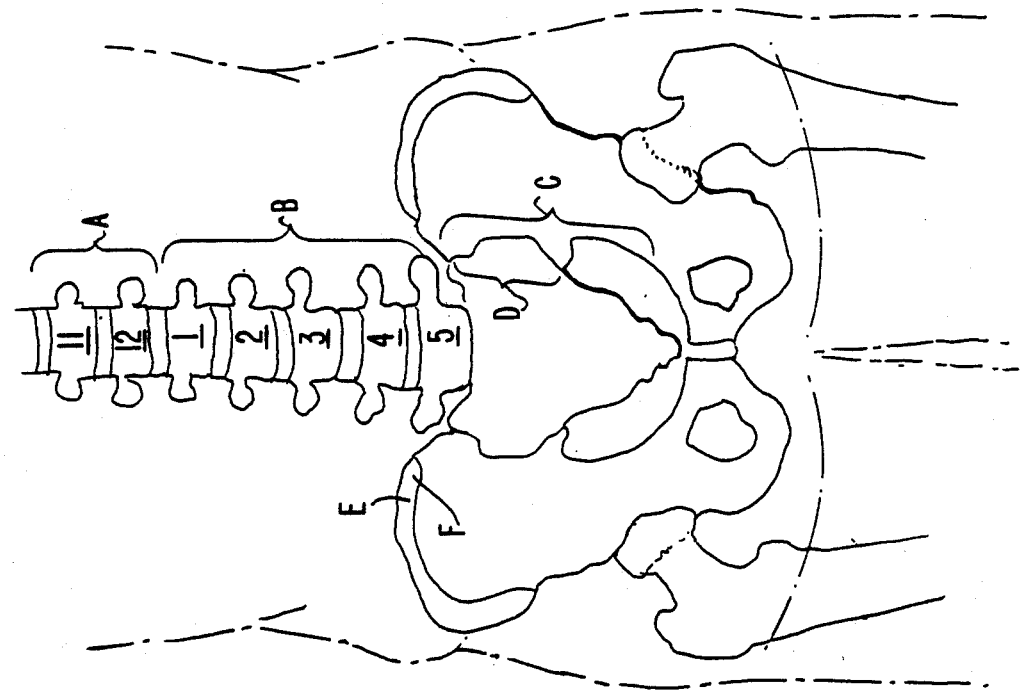
FIG. 2 illustrates a cut-away view of the device according to the present invention showing the relationship of the air bladder to the lumbosacral spine and sacroiliac joints.

The therapeutic appliance of the present invention is generally indicated at 10 in FIGS. 2 and 4. FIG. 1 illustrates the areas anatomically underlying the therapeutic appliance. These areas are those intended to be therapeutically affected by the appliance. The lumbar spine (B) consists of five vertebrae in normal subjects, each separated by an intervening intervertebral disc. The sacrum (C) consist of five anatomically fused segments. The sacroiliac joints (D) represents the articulation of the sacrum and iliac bones on each side. The iliac crest (E) is that portion of the iliac bone lying highest and ending in the posterior superior iliac spine (F) which is the most posterior bony protuberence. Both (E) and (F) may hold prior art appliances away from the spine and paravertebral musculature to be treated thus diminishing the intended therapeutic counter-pressure.

The therapeutic appliance of the present invention comprises a belt and an air bladder 11 which includes a number of air chambers shown generally at 11a and a non-air filled segment 1 of the bladder, as shown in FIG. 2. The air chambers comprise central transversely extending air chambers 2 which overlie the midline of the lumbar spine and which extend vertically down to the sacrum. On either side of the central air chambers 2 are more laterally placed air chambers 3 which have lower ends which extend in an arcuate path and follow the contour of the iliac crests. The upper ends of the air chambers 2 and 3 are substantially parallel to each other. Below the central air chambers 2 are longitudinally extending air chambers 4 which overlie the sacrum and lie between the sacroiliac joints and arcuately extending air chambers 4A which overlie the sacroiliac joints and which lie just beneath the posterior superior iliac spines and serve additionally as anchors to prevent upward riding of the appliance and also provide support for the sacroiliac joints. The air chambers are separated by a heat sealed or sewn portion of the bladder material. It can be seen from FIGS. 4a and 4b that the bladder 1 extends around a shell 7 of the therapeutic device terminating short of a closure device 8. The air chambers are shown generally at 11a in a rear portion of the therapeutic device, as shown in FIGS. 4a and 4b. The contoured fit of the air chambers when inflated are shaped to maintain the normal lordotic curvature of an individual wearer's spine as can be seen in FIG. 3.

Figure 4A:
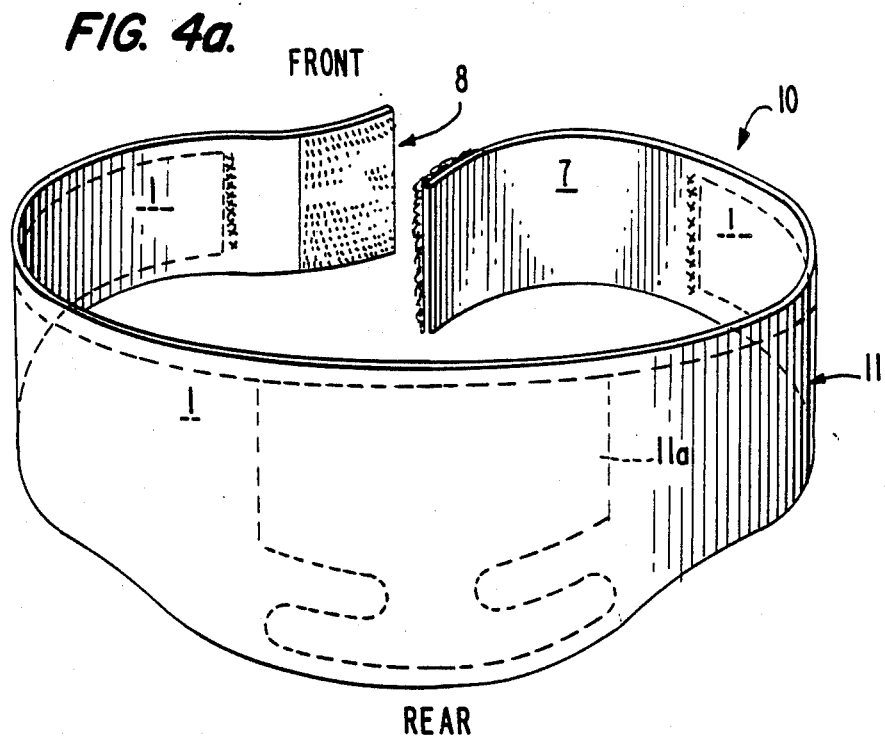
FIG. 4a shows a perspective view of the device according to the present invention with an external shell enclosing the air bladder.
Figure 4B:
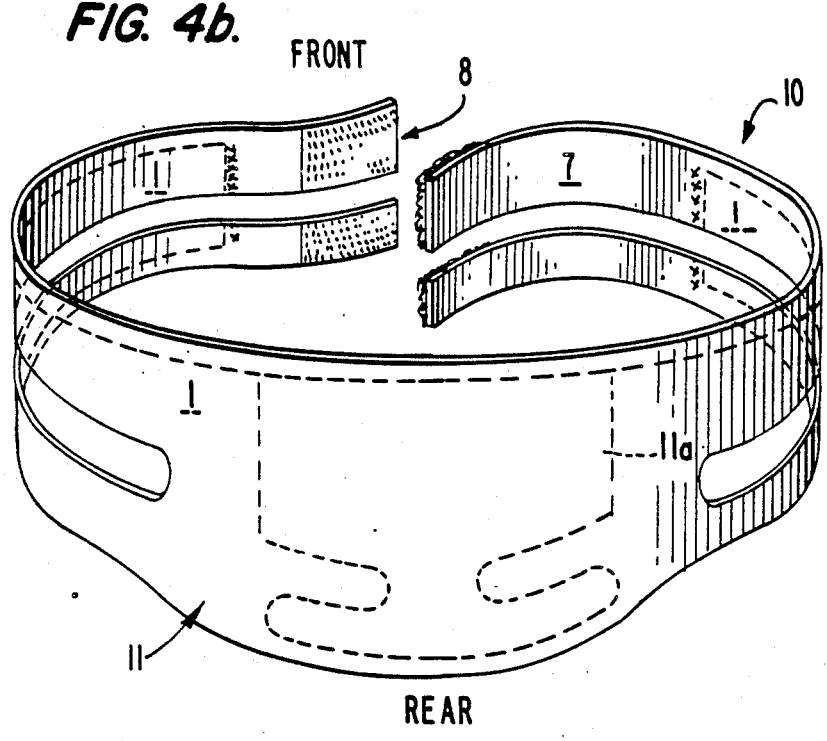
FIG. 4b shows a perspective view of another embodiment of the device according to the present invention with the external shell being separated into two elongated sections on either side of the air bladder.
Figure 5B:
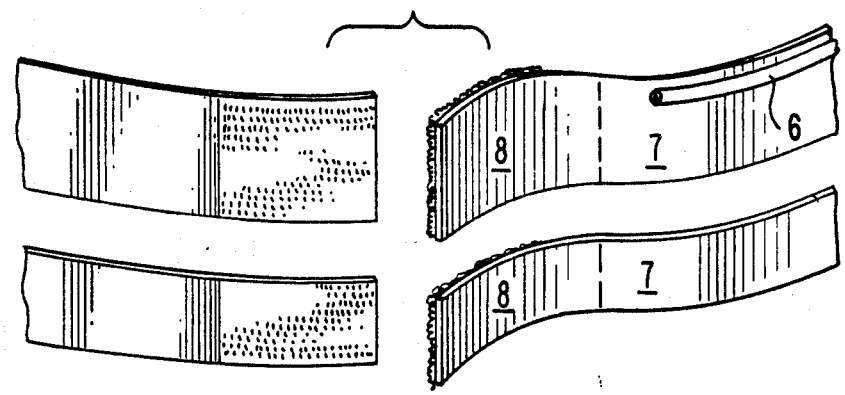
FIG. 5b is a perspective view of the device shown in FIG. 4b which shows the outlet for an air conduit located near an upper front closure.
Figure 5A:
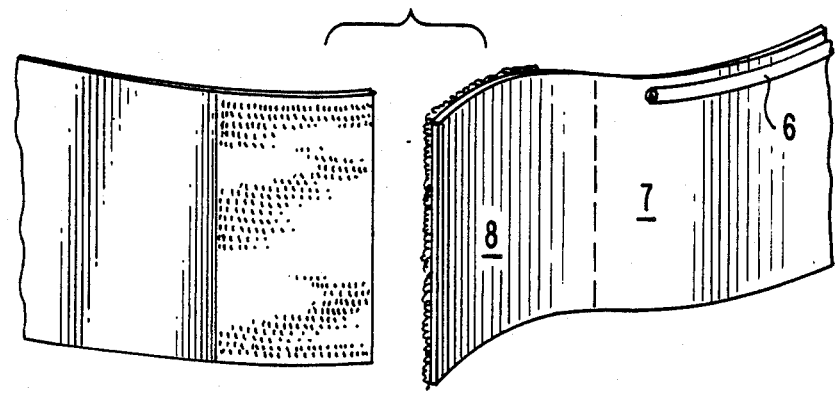
FIG. 5a is a perspective view of the device according to the present invention which shows the outlet for an air conduit located near the front closure.

The external shell 7 of the therapeutic device of the present invention is composed of a washable moisture absorbent fabric which allows the device to be worn inside or outside of the wearer's clothing. The external shell 7 assumes the same basic shape of the contained air bladder 1 which it protects. The bladder 1 is fabricated from a nylon or plastic/vinyl material with low stretchability to allow repeated reproduction of the same air chamber configuration each time the air chambers are inflated. The therapeutic appliance can be secured over the wearer's trunk by a single closure device 8 which can be a VELCRO type of attachment, as shown in FIGS. 4a and 5a, or the external shell can be separated into an upper and lower section which extend longitudinally from adjacent the bladder 1 with a space therebetween and with a closure device at the free end of each section, as shown in FIGS. 4b and 5b. Alternatively, other fastening means such as buckles, snaps or lace-up type of attachment means can be used.

Figure 3:
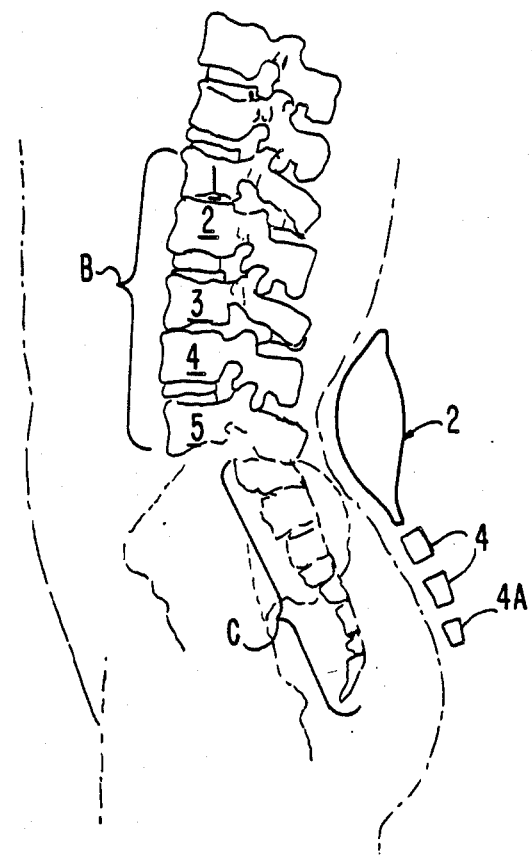
FIG. 3 shows a side view of the spine and the positions of the air chambers of the device according to the present invention.

FIG. 3 shows a midline sagital section of the inflated central air chambers having a tapered upper and lower end with a broad central section of the vertically aligned lumbar chamber intended to aid in the maintenance of the normal lumbar lordotic curvature. Alternatively, other configurations of the inflated air chambers are within the scope of the present invention.

Figure 6:
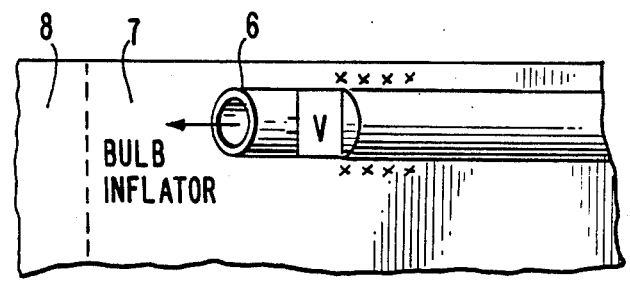

FIG. 5a shows the position of an air conduit 6 in the upper margin of the external shell 7 where it exits to the external surface of the shell or the air conduit can be located in the upper section of the external shell, as shown in FIG. 5b. However, the air conduit 6 can be located anywhere within the bladder 11. An enlarged drawing of the outlet of the air conduit 6 is shown in FIG. 6 wherein a valve (V) is shown within the air conduit for maintaining inflation at a desired level. Also, not show is an air pump, such as a bulb inflater, which can be attached to the outlet of the air conduit 6 for inflation of the air chambers.

Figure 7:
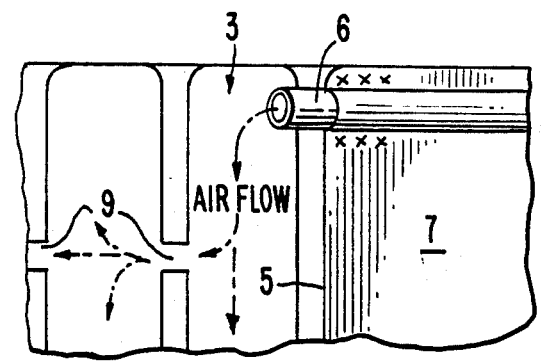
FIG. 7 is a cut-away view showing the connection of the air conduit to the air chambers.

FIG. 7 shows the entry of the air conduit 6 into the laterally placed chamber 3. The air conduit 6 is held in position within the bladder 11 and in fluid communication with at least one of the air chambers 11a by heat sealing or sewing a segment 5 of the air bladder 1. Air passes freely from the air conduit 6 into one of the air chambers, such as a lateral chamber 3, and then through openings 9 between the air chambers for allowing the air to fill all chambers within the bladder.

The preceding specific embodiment is illustrative of the practice of the invention. It is to be understood, however, that other expedients known to those skilled in the art or disclosed herein, may be employed without departing from the spirit of the invention or the scope of the appended claims.

We claim:

1. A therapeutic appliance for application to the lumbar spine and which follows the contours of the iliac crests and overlies the sacrum and sacroiliac joints as well as anchors below the posterior superior iliac spines of the human body, the appliance comprising:

an external shell having a length in a longitudinal direction sufficient to extend around and encircle the abdominal region of the body, said shell having closure means at opposite ends thereof for attaching said ends together;

an air bladder disposed on said external shell, said air bladder having a plurality of air chambers located centrally between said opposite ends of said shell, said air chambers including elongated air chambers which extend transversely to said longitudinal direction, said air chambers each having a lower end, the lower ends extending in an arcuate path on each side of a central portion of said air bladder, said arcuate path being shaped to lie above the iliac crests, and at least one anchoring air chamber extending arcuately between said lower ends of said transversely extending air chambers and a longitudinally extending outer edge of said bladder, said anchoring air chamber extending from said central portion of said air bladder toward said opposite ends of said shell and positioned to lie below the posterior superior iliac spines to prevent upward riding of said therapeutic appliance when inflated and in place on the human body and provide support to the sacroiliac joints; and air conduit means for inflating said air chambers with air.

2. The therapeutic appliance of claim 1, wherein the at least one anchoring air chamber comprises a pair of arcuately extending air chambers each of which extends towards a respective one of said opposite ends of said external shell.

3. The therapeutic appliance of claim 1, wherein said transversely extending air chambers have upper ends which are substantially parallel to each other.

4. The therapeutic appliance of claim 1, wherein said air bladder is a plastic material having low stretchability to allow accurate reproduction of the configurations of said air chambers, each of said air chambers being separated by a joint between an inner and outer layer of said air bladder.

5. The therapeutic appliance of claim 4, wherein said joint is a heat seal between said inner and outer layer of plastic.

6. The therapeutic appliance of claim 4, wherein said joint is a sewn seam between said inner and outer layer of plastic.

7. The therapeutic appliance of claim 1, wherein said shell is a washable moisture absorbent fabric material.

8. The therapeutic appliance of claim 1, wherein said air conduit means includes an air conduit having a valve at an outlet end thereof, said outlet end being adapted for connection to an air pump for filling said air chambers with air.

9. The therapeutic appliance of claim 1, wherein said external shell is divided on each side of said air bladder into an upper and a lower longitudinally extending section with a space therebetween, said upper section and said lower section each having a closure means at a free end thereof.

10. A therapeutic appliance for application to the lumbar spine and which follows the contours of the iliac crests and overlies the sacrum and sacroiliac joints as well as anchors below the posterior superior iliac spines of the human body, the appliance comprising:

an external shell having a length in a longitudinal direction sufficient to extend around and encircle the abdominal region of the body, said shell having closure means at opposite ends thereof for attaching said ends together;

an air bladder disposed on said external shell, said air bladder having a plurality of air chambers located centrally between said opposite ends of said shell, said air chambers including elongated air chambers which extend transversely to said longitudinal direction, said air chambers each having a lower end, the lower ends extending in an arcuate path on each side of a central portion of said air bladder, said arcuate path being shaped to lie above the iliac crests, at least one elongated air chamber which extends in said longitudinal direction and which is disposed between said lower ends of said transversely extending air chambers and a longitudinally extending outer edge of said bladder, said longitudinally extending air chamber positioned to overlie the sacrum and sacroiliac joints, and at least one anchoring air chamber extending arcuately between said longitudinally extending air chamber and said outer edge of said bladder, said anchoring air chamber extending from said central portion of said air bladder toward said opposite ends of said shell and positioned to lie below the posterior superior iliac spines to prevent upward riding of said therapeutic appliance when inflated and in place on the human body and provide support to the sacroiliac joints; and air conduit means for inflating said air chambers with air.

11. The therapeutic appliance of claim 10, wherein the at least one anchoring air chamber comprises a pair of arcuately extending air chambers each of which extends towards a respective one of said opposite ends of said external shell.

12. The therapeutic appliance of claim 10, wherein said at least one longitudinally extending air chamber comprises a pair of air chambers which are spaced apart from each other in a direction transverse to said longitudinal direction.

13. The therapeutic appliance of claim 10, wherein said air bladder is a plastic material having low stretchability to allow accurate reproduction of the configurations of said air chambers, each of said air chambers being separated by a joint between an inner and outer layer of said air bladder.

14. The therapeutic appliance of claim 13, wherein said joint is a heat seal between said inner and outer layer of plastic.

15. The therapeutic appliance of claim 13, wherein said joint is a sewn seam between said inner and outer layer of plastic.

16. The therapeutic appliance of claim 10, wherein said shell is a washable moisture absorbent fabric material.

17. The therapeutic appliance of claim 10, wherein said air conduit means includes an air conduit having a valve at an outlet end thereof, said outlet end being adapted for connection to an air pump for filling said air chambers with air.

18. The therapeutic appliance of claim 10, wherein said transversely extending air chambers have upper ends which are substantially parallel to each other.

19. The therapeutic appliance of claim 10, wherein said external shell is divided on each side of said air bladder into an upper and a lower longitudinally extending section with a space therebetween, said upper section and said lower section each having a closure means at a free end thereof.

20. A therapeutic appliance for application to the lumbar spine and which follows the contours of the iliac crests and overlies the sacrum and sacroiliac joints as well as anchors below the posterior superior iliac spines of the human body, the appliance comprising:

an external shell having a length in a longitudinal direction sufficient to extend around and encircle the abdominal region of the body, said shell having closure means at opposite ends thereof for attaching said ends together;

an air bladder disposed on said external shell, said air bladder having a plurality of air chambers located centrally between said opposite ends of said shell, said air chambers including elongated air chambers which extend transversely to said longitudinal direction, said air chambers each having a lower end, the lower ends extending in an arcuate path on each side of a central portion of said air bladder, said arcuate path being shaped to lie above the iliac crests, and anchoring air chamber means for preventing upward riding of said therapeutic appliance when said air bladder is inflated and in place on a human body and providing support to the sacroiliac joints, said anchoring air chamber means comprising at least one anchoring air chamber extending arcuately between said lower ends of said transversely extending air chambers and a longitudinally extending outer edge of said bladder, said anchoring air chamber means extending from said central portion of said air bladder toward said opposite ends of said shell and positioned to lie below the posterior superior iliac spines; and air conduit means for inflating said air chambers with air.

* * * * *